(12) United States Patent
Ostroot et al.

(10) Patent No.: US 11,992,260 B2
(45) Date of Patent: May 28, 2024

(54) SMART PROBE IDENTIFICATION FOR ABLATION MODALITIES

(71) Applicant: Boston Scientific Scimed, Inc., Maple Grove, MN (US)

(72) Inventors: Timothy A. Ostroot, Cokato, MN (US); Bruce R. Forsyth, Hanover, MN (US); Hong Cao, Maple Grove, MN (US); Larry D. Canady, Jr., Ham Lake, MN (US); Jonathan Tyler Gorzycki, Blaine, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 193 days.

(21) Appl. No.: 17/216,871

(22) Filed: Mar. 30, 2021

(65) Prior Publication Data

US 2021/0298822 A1 Sep. 30, 2021

Related U.S. Application Data

(60) Provisional application No. 63/002,991, filed on Mar. 31, 2020.

(51) Int. Cl.
*A61B 18/14* (2006.01)
*A61B 18/00* (2006.01)
(Continued)

(52) U.S. Cl.
CPC ...... *A61B 18/1492* (2013.01); *A61B 18/1206* (2013.01); *G16H 40/67* (2018.01);
(Continued)

(58) Field of Classification Search
CPC ............ A61B 18/1492; A61B 18/1206; A61B 2018/00577; A61B 2018/00779;
(Continued)

(56) References Cited

U.S. PATENT DOCUMENTS 5,019,034 A  5/1991  Weaver et al.
5,370,675 A  12/1994 Edwards et al.
(Continued)

FOREIGN PATENT DOCUMENTS

JP  H11346436 A  12/1999
WO  2008102154 A2  8/2008
WO  2015021113 A1  2/2015

OTHER PUBLICATIONS

StarBurst XL RFA Electrodes, Angiodynamics Inc. 2013. 2 pages.
(Continued)

*Primary Examiner* — Linda C Dvorak
*Assistant Examiner* — Abigail Bock
(74) *Attorney, Agent, or Firm* — Seager, Tufte & Wickhem LLP

(57) ABSTRACT

Ablation probes and methods of their use. Example probes include probe circuits configured to provide identifying information for the probe itself. The probe circuits may sense probe usage and/or age to determine probe end of life (EOL). In response to EOL, the probe circuit generates an output indicating EOL. The probe electronic circuit may also be configured to monitor probe usage via impedance or other features, independent of such operation by an ablation pulse generator.

6 Claims, 11 Drawing Sheets

(51) Int. Cl.
    *A61B 18/12* (2006.01)
    *G16H 40/67* (2018.01)
(52) U.S. Cl.
    CPC .............. *A61B 2018/00577* (2013.01); *A61B 2018/00779* (2013.01); *A61B 2018/00827* (2013.01); *A61B 2018/00892* (2013.01); *A61B 2018/1467* (2013.01)
(58) Field of Classification Search
    CPC ........... A61B 2018/00827; A61B 2018/00892; A61B 2018/1467; G16H 40/67
    See application file for complete search history.

(56) References Cited

U.S. PATENT DOCUMENTS

| | | | |
|---|---|---|---|
| 5,718,246 | A | 2/1998 | Vona |
| 5,855,576 | A | 1/1999 | Leveen et al. |
| 5,863,290 | A | 1/1999 | Gough et al. |
| 6,010,613 | A | 1/2000 | Walters et al. |
| 6,041,252 | A | 3/2000 | Walker et al. |
| 6,043,066 | A | 3/2000 | Mangano et al. |
| 6,278,895 | B1 | 8/2001 | Bernard |
| 6,326,177 | B1 | 12/2001 | Schoenbach et al. |
| 6,387,671 | B1 | 5/2002 | Rubinsky et al. |
| 6,428,534 | B1 | 8/2002 | Joye et al. |
| 6,638,277 | B2 | 10/2003 | Schaefer et al. |
| 6,714,816 | B1 | 3/2004 | Heller et al. |
| 6,911,027 | B1 | 6/2005 | Edwards et al. |
| 6,912,471 | B2 | 6/2005 | Heigl et al. |
| 6,994,706 | B2 | 2/2006 | Chornenky et al. |
| 7,245,963 | B2 | 7/2007 | Draghia-Akli et al. |
| 7,306,595 | B2 | 12/2007 | Ostrovsky et al. |
| 7,306,940 | B2 | 12/2007 | Miklavcic et al. |
| 7,416,549 | B2 | 8/2008 | Young et al. |
| 7,456,012 | B2 | 11/2008 | Ryttsn et al. |
| 7,794,458 | B2 | 9/2010 | Mcintyre et al. |
| 7,799,022 | B2 | 9/2010 | Fernald et al. |
| 7,850,681 | B2 | 12/2010 | Lafontaine |
| 8,014,854 | B2 | 9/2011 | Schroeppel et al. |
| 8,048,067 | B2 | 11/2011 | Davalos et al. |
| 8,114,070 | B2 | 2/2012 | Rubinsky et al. |
| 8,152,801 | B2 | 4/2012 | Goldberg et al. |
| 8,211,104 | B2 | 7/2012 | Mccullagh et al. |
| 8,251,986 | B2 | 8/2012 | Chornenky et al. |
| 8,282,631 | B2 | 10/2012 | Davalos et al. |
| 8,465,484 | B2 | 6/2013 | Davalos et al. |
| 8,540,710 | B2 | 9/2013 | Johnson et al. |
| 8,603,087 | B2 | 12/2013 | Rubinsky et al. |
| 8,647,338 | B2 | 2/2014 | Chornenky et al. |
| 8,801,709 | B2 | 8/2014 | Prakash et al. |
| 8,915,911 | B2 | 12/2014 | Azure |
| 8,920,416 | B2 | 12/2014 | Pham et al. |
| 8,926,606 | B2 | 1/2015 | Davalos et al. |
| 9,005,189 | B2 | 4/2015 | Davalos et al. |
| 9,168,096 | B2 | 10/2015 | Kreindel |
| 10,105,172 | B2 | 10/2018 | Johnson et al. |
| 10,154,869 | B2 | 12/2018 | Onik et al. |
| 10,238,447 | B2 | 3/2019 | Nea, II et al. |
| 10,548,660 | B2 | 2/2020 | Janssen et al. |
| 11,045,648 | B2 | 6/2021 | Dewitt et al. |
| 2001/0044596 | A1 | 11/2001 | Jaafar |
| 2002/0107515 | A1 | 8/2002 | Edwards et al. |
| 2002/0115991 | A1 | 8/2002 | Edwards |
| 2003/0009110 | A1 | 1/2003 | Tu et al. |
| 2004/0015163 | A1 | 1/2004 | Buysse et al. |
| 2004/0186468 | A1 | 9/2004 | Edwards |
| 2005/0267467 | A1 | 12/2005 | Paul et al. |
| 2005/0283148 | A1* | 12/2005 | Janssen .................. A61B 18/16 606/50 |
| 2006/0142801 | A1 | 6/2006 | Demarais et al. |
| 2006/0293730 | A1 | 12/2006 | Rubinsky et al. |
| 2007/0025919 | A1 | 2/2007 | Deem et al. |
| 2008/0275445 | A1 | 11/2008 | Kelly et al. |
| 2009/0247933 | A1 | 10/2009 | Maor et al. |
| 2009/0254148 | A1* | 10/2009 | Borgens .................. A61N 1/326 607/50 |
| 2009/0306639 | A1* | 12/2009 | Nevo ...................... G16H 40/67 705/2 |
| 2009/0326638 | A1 | 12/2009 | Atanasoka et al. |
| 2010/0023004 | A1 | 1/2010 | Francischelli et al. |
| 2010/0261994 | A1 | 10/2010 | Davalos et al. |
| 2011/0170321 | A1 | 7/2011 | Schall et al. |
| 2011/0238057 | A1 | 9/2011 | Moss et al. |
| 2012/0053403 | A1 | 3/2012 | Ducharme et al. |
| 2012/0197356 | A1 | 8/2012 | Wei et al. |
| 2012/0310230 | A1 | 12/2012 | Willis |
| 2012/0330299 | A1 | 12/2012 | Webster et al. |
| 2013/0046292 | A1 | 2/2013 | Janssen et al. |
| 2013/0184702 | A1 | 7/2013 | Neal, II et al. |
| 2014/0025066 | A1* | 1/2014 | Kerr ........................ G01L 1/246 606/34 |
| 2014/0121663 | A1 | 5/2014 | Pearson et al. |
| 2014/0128859 | A1 | 5/2014 | Lee |
| 2014/0128936 | A1 | 5/2014 | Laufer et al. |
| 2016/0058493 | A1 | 3/2016 | Neal, II et al. |
| 2016/0113709 | A1 | 4/2016 | Maor |
| 2016/0199661 | A1 | 7/2016 | Willard et al. |
| 2017/0035499 | A1 | 2/2017 | Stewart |
| 2017/0105793 | A1 | 4/2017 | Cao et al. |
| 2017/0245928 | A1 | 8/2017 | Xiao et al. |
| 2018/0250508 | A1 | 9/2018 | Howard |
| 2018/0272124 | A1 | 9/2018 | Kibler et al. |
| 2018/0303543 | A1 | 10/2018 | Srewart et al. |
| 2019/0143106 | A1 | 5/2019 | Dewitt et al. |
| 2019/0223943 | A1 | 7/2019 | Forsyth et al. |
| 2020/0085531 | A1* | 3/2020 | Harrison ................. A61B 90/90 |
| 2020/0129230 | A1 | 4/2020 | Forsyth et al. |
| 2020/0155227 | A1 | 5/2020 | Cao et al. |
| 2020/0289185 | A1 | 9/2020 | Forsyth et al. |
| 2020/0289188 | A1 | 9/2020 | Forsyth et al. |
| 2020/0289827 | A1 | 9/2020 | Forsyth et al. |
| 2021/0106374 | A1 | 4/2021 | Forsyth et al. |

OTHER PUBLICATIONS

Deodhar et al; "Irreversible Electroporation Near the Heart: Ventricular Arrhythmias Can Be Prevented With ECG Synchronization." AJR 196:W330-W335, Mar. 2011. Accessed on Jul. 16, 2019.
Beebe et al; "Nanosecond Pulsed Electric Field (nsPEF) Effects on Cells and Tissues: Apoptosis Induction and Tumor Growth Inhibition", IEEE Transactions on Plasma Science, 6 pages, Mar. 2002.
Kennedy et al; "Cationic Peptide Exposure Enhances Pulsed-Electric-Field-Mediated Membrane Disruption", PLOS ONE, vol. 9, Issue 3, 17 pp. Mar. 2014.
Miklavcic et al; "The Importance of Electric Field Distribution for Effective in Vivo Electroporation of Tissues", Biophysical Journal, vol. 74, pp. 2152-2158, May 1998.
Distelmaier et al; "Midterm Safety and Efficacy of Irreversible Electroporation of Malignant Tumors Located Close to Major Portal or Hepatic Veins", Radiology, vol. 285, No. 3, 1023-1031, Dec. 2017.
Rubinsky et al; "Irreversible Electroporation: A New Ablation Modality—Clinical Implications." Technology in Cancer Research and Treatment, vol. 6, No. 1, pp. 37-48, Feb. 2007.
Swartz et al; "Sparking New Frontiers: Using in Vivo Electroporation for Genetic Manipulations", Developmental Biology, 233, pp. 13-21, 2001.
Tsong, "Electroporation of Cell Membranes," Biophysical Journal, vol. 60, pp. 297-306, Aug. 2, 1991.
International Search Report and Written Opinion dated Jul. 2, for International Application No. PCT/US2020/022582.
International Search Report and Written Opinion Dated Jul. 7, 2020 for International Application No. PCT/US2020/022571.
Invitation to Pay Additional Fees dated Jan. 28, 2021 for International Application No. PCT/US2020/055577.

* cited by examiner

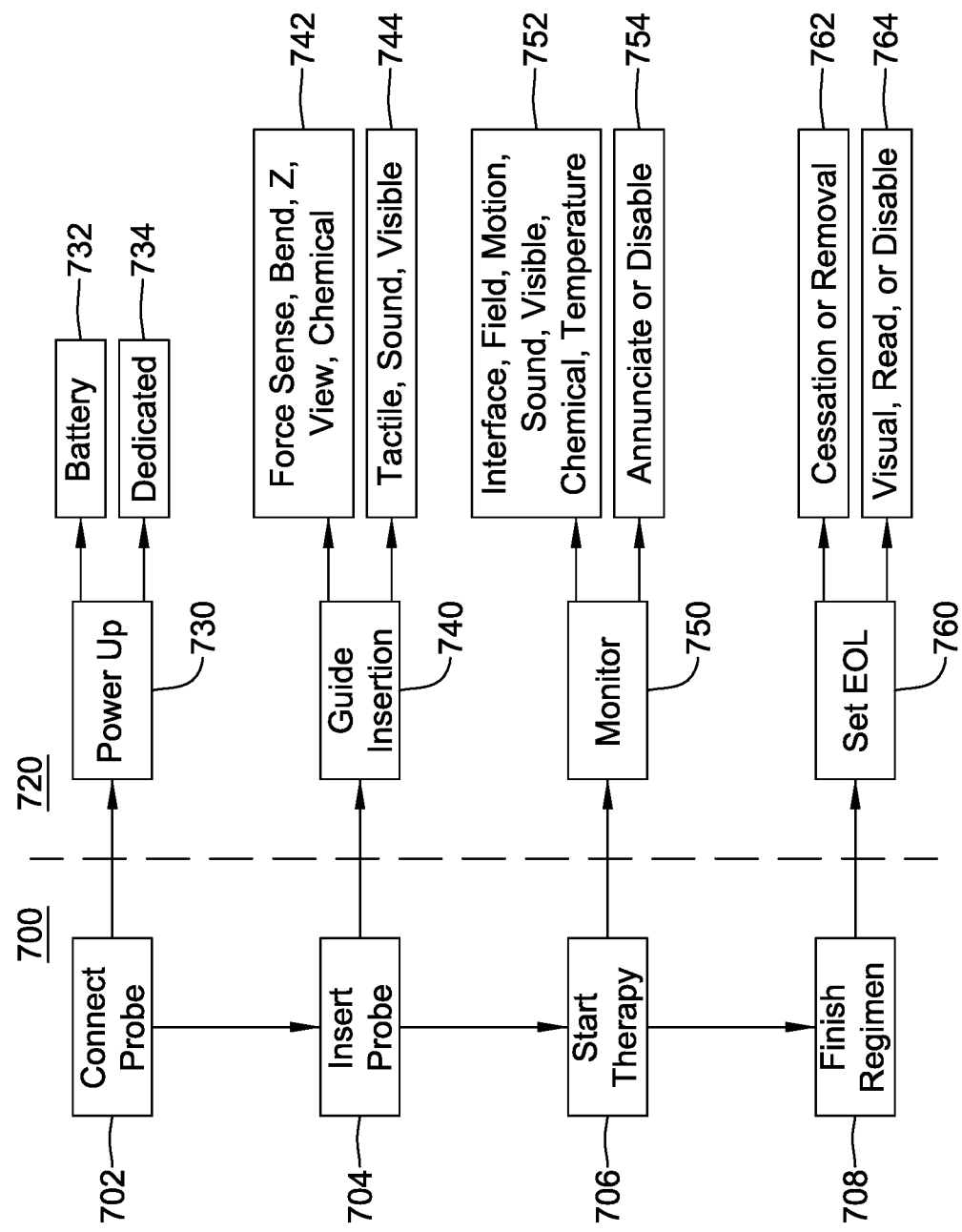

SMART PROBE IDENTIFICATION FOR ABLATION MODALITIES

CROSS REFERENCE TO RELATED APPLICATIONS

This application claims the benefit of and priority to U.S. Provisional Patent Application Ser. No. 63/002,991 filed on Mar. 31, 2020, the disclosure of which is incorporated herein by reference.

BACKGROUND

Removal or destruction of diseased tissue is a goal of many cancer treatment methods. Tumors may be surgically removed, however, less invasive approaches garner much attention. Tissue ablation is a minimally invasive method of destroying undesirable tissue in the body. A variety of ablation techniques have been developed, many using the application of electricity or other energy via a probe placed on or inserted into or adjacent target tissue. For example, heat-based thermal ablation adds heat to destroy tissue, while cold ablation does the opposite, resulting in cell death by the application of cold temperatures. Radio-frequency (RF) thermal, microwave and high intensity focused ultra-sound ablation can each be used to raise localized tissue temperatures well above the body's normal 37 degrees C., destroying tissue with heat. Irreversible electroporation (IRE) uses electric fields to expand pores in the cell membrane beyond the point of recovery, causing cell death for want of a patent cell membrane. IRE typically uses a narrower pulse width than RF ablation to reduce thermal effects.

Ablation is typically performed using a probe or probes that are placed in or in proximity to target tissue. New and alternative probes that can facilitate system configuration and/or enhance reliability or surgical monitoring processes are desired.

Overview

The present inventors have recognized, among other things, that a problem to be solved is the need for new and/or alternative ablation probes. In some examples, a probe contains electronic features that allow a pulse generator to identify the probe, either by using a device identifier (that the pulse generator may look up) or by providing configuration data (number and size or electrodes, for example) as stored data. In some examples a probe contains one or more features to ensure single use only, or that identify, to the pulse generator, probe end of life. In some examples, a probe also provides feedback to the user, separate from a pulse generator user interface, regarding probe type, status, faults, or other data.

A first illustrative and non-limiting example takes the form of an ablation probe configured for use with an ablation generator, comprising: a distal end having one or more electrodes thereon for delivering therapy directed at target tissue; a proximal end having one or more contacts thereon for coupling to the ablation generator; an elongated body between the proximal and distal ends carrying at least one conductor that electrically couples at least one electrode to at least one contact; and a probe electronic circuit in or on the probe and configured to sense usage of the probe, determine a status of the probe relative to a predetermined end of life for the probe, and generate an output related to the determined status.

Additionally or alternatively, the probe electronic circuit is coupled to a sensor for sensing at least one of a voltage or current in the at least one conductor. Additionally or alternatively, the probe electronic circuit is configured to record at least one of a voltage, a quantity of therapy pulses, a quantity of current or charge, or a quantity of energy or power delivered by the probe. Additionally or alternatively, the probe electronic circuit is coupled to one or more electrodes adapted for sensing a status or condition at the distal end of the lead by one of the at least one conductor in the elongated body.

Additionally or alternatively, the probe electronic circuit is coupled to an antenna configured for use in passive communication in which the antenna and probe electronic circuit respond to a wireless interrogation signal, wherein the probe electronic circuit is configured to manipulate the response to the interrogation signal based on probe usage. Additionally or alternatively, the probe electronic circuit is coupled to a power supply independent of the ablation generator.

Additionally or alternatively, the probe power supply is configured to provide power to the probe electronic circuit at least before the probe is used, and the probe further comprises an external indicator coupled to the probe electronic circuit; wherein the probe electronic circuit is configured to determine end of life based on failure to use the probe before a use-by date, and, in response to determining end of life for failure to use by the use-by date, to manipulate the external indicator to show the probe is not fit for use.

Additionally or alternatively, the probe electronic circuit is configured to disable use of the probe in response to probe end of life. Additionally or alternatively, the ablation probe may further comprise a probe circuit power supply configured to obtain power from the ablation generator via a dedicated power supply line. Additionally or alternatively, the ablation probe may further comprise a probe circuit power supply configured to obtain power from the ablation generator by obtaining power from the one or more conductors when signals are issued by the ablation generator for delivery via the electrodes.

Additionally or alternatively, the probe electronic circuit is configured to measure or determine impedance at or near the distal end of the probe. Additionally or alternatively, the probe electronic circuit is coupled, via a dedicated conductor, to the probe proximal end, which in turn includes a dedicated contact for enabling the data to be transmitted to the ablation generator.

Additionally or alternatively, the ablation probe may further comprise an electronic indicator providing visual feedback to a user of the probe, the electronic indicator being located on the probe and separate from a user interface of the ablation generator, wherein the electronic circuit is coupled to the electronic indicator to allow the data to be displayed to a user via the electronic indicator.

Additionally or alternatively, the probe electronic circuit comprises at least one of a voltage sensor and a current sensor coupled to the at least one conductor, and the probe electronic circuit is configured, using signal sensed by the at least one voltage or current sensor, to detect a fault in the probe and to control the electronic indicator to provide an indication of whether the fault is present.

A second illustrative and non-limiting example takes the form of an ablation probe configured for use with an ablation generator, comprising: a distal end having one or more electrodes thereon for delivering therapy directed at target tissue; a proximal end having one or more contacts thereon for coupling to the ablation generator; an elongated body between the proximal and distal ends carrying at least one conductor that electrically couples at least one electrode to at least one contact; and a probe electronic circuit in or on the probe and configured to sense usage of the probe, determine a status of the probe relative to a predetermined end of life for the probe, and generate an output related to the determined status.

Additionally or alternatively, the probe electronic circuit is coupled to a sensor for sensing at least one of a voltage or current in the at least one conductor. Additionally or alternatively, the probe electronic circuit is configured to record at least one of a voltage, a quantity of therapy pulses, a quantity of current or charge, or a quantity of energy or power delivered by the probe. Additionally or alternatively, the probe electronic circuit is coupled to one or more electrodes adapted for sensing a status or condition at the distal end of the lead by one of the at least one conductor in the elongated body. Additionally or alternatively, the proximal end comprises at least one contact for linking the ablation generator to the probe electronic circuit, wherein the probe electronic circuit is configured to generate the output to the ablation generator. Additionally or alternatively, the probe electronic circuit is coupled to an antenna to facilitate wireless communication between the probe electronic circuit and the ablation signal generator.

Additionally or alternatively, the probe electronic circuit is coupled to an antenna configured for use in passive communication in which the antenna and probe electronic circuit respond to a wireless interrogation signal, wherein the probe electronic circuit is configured to manipulate the response to the interrogation signal based on probe usage.

Additionally or alternatively, the probe electronic circuit is coupled to a power supply independent of the ablation generator.

Additionally or alternatively, the ablation probe may further comprise a probe power supply independent of the ablation generator and coupled to the probe electronic circuit to provide power thereto at least before the probe is used; and an external indicator coupled to the probe electronic circuit; wherein the probe electronic circuit is configured to determine end of life based on failure to use the probe before a use-by date, and, in response to determining end of life for failure to use by the use-by date, to manipulate the external indicator to show the probe is not fit for use.

Additionally or alternatively, the probe electronic circuit is configured to disable use of the probe in response to probe end of life.

A third illustrative and non-limiting example takes the form of an ablation probe configured for use with an ablation generator, comprising: a distal end having one or more electrodes thereon for delivering therapy directed at target tissue; a proximal end having one or more contacts thereon for coupling to the ablation generator; an elongated body between the proximal and distal ends carrying at least one conductor that electrically couples at least one electrode to at least one contact; a probe electronic circuit in or on the probe and configured to obtain power from the ablation generator and sense one or more characteristics of usage of the probe, quantify the one or more characteristics, and record or transmit data related to the sensed and quantified one or more characteristics.

Additionally or alternatively, the probe electronic circuit is configured so that the one or more characteristics includes end of life of the probe.

Additionally or alternatively, the probe electronic circuit is configured so that the one or more characteristics includes impedance at or near the distal end of the probe.

Additionally or alternatively, the probe electronic circuit comprises or is coupled to an antenna for wirelessly transmitting the data.

Additionally or alternatively, the probe electronic circuit is coupled, via a dedicated conductor, to the probe proximal end, which in turn includes a dedicated contact for enabling the data to be transmitted to the ablation generator.

Additionally or alternatively, the ablation probe may further comprise an electronic indicator providing visual feedback to a user of the probe, the electronic indicator being located on the probe and separate from a user interface of the ablation generator, wherein the electronic circuit is coupled to the electronic indicator to allow the data to be displayed to a user via the electronic indicator.

Additionally or alternatively, the electronic circuit obtains power from the ablation generator by drawing power from signals transmitted to the distal end of the probe by the conductor.

Additionally or alternatively, the electronic circuit obtains power from the ablation generator via a dedicated connection to the ablation generator.

A fourth illustrative and non-limiting example takes the form of a probe configured for use with an ablation generator, comprising: a distal end having one or more electrodes thereon for delivering therapy directed at target tissue; a proximal end having one or more contacts thereon for coupling to the ablation generator; an elongated body between the proximal and distal ends carrying at least one conductor that electrically couples at least one electrode to at least one contact; and an electronic indicator providing visual feedback to a user of the probe, the electronic indicator being located on the probe and separate from a user interface of the ablation generator.

Additionally or alternatively, the ablation probe may further comprise an electronic circuit coupled to the electronic indicator and configured to sense usage of the probe, determine when the probe has reached a predetermined end of life, and control the electronic indicator to provide visual feedback to the user indicating end of life.

Additionally or alternatively, the ablation probe may further comprise an electronic circuit coupled to the electronic indicator and configured to sense usage of the probe, determine a status of the probe relative to a predetermined end of life, and control the electronic indicator to provide visual feedback to the user indicating status of the probe relative to end of life.

Additionally or alternatively, the electronic circuit includes or is coupled to a current sensor configured to sense current through the at least one conductor to thereby sense usage of the probe.

Additionally or alternatively, the proximal end comprises a manifold for securing to the ablation generator, and the electronic indicator is on the manifold.

Additionally or alternatively, the ablation probe may further comprise a handle on the elongated body between the proximal and distal ends adapted to be held by a user thereof, wherein the electronic indicator is proximal of the handle.

Additionally or alternatively, the electronic indicator is an LCD or LED screen. Additionally or alternatively, the electronic indicator comprises a plurality of lights. Additionally or alternatively, the ablation probe may further comprise an electronic circuit adapted to determine whether an electrical signal is being transmitted via the at least one conductor and to control the electronic indicator to provide an indication of whether the probe is active. Additionally or alternatively, the ablation probe may further comprise an electronic circuit adapted to sense at least one of voltage and current in the at least one conductor, to determine whether the sensed at least one of voltage and current indicates a fault, and to control the electronic indicator to provide an indication of whether the fault is present.

Additionally or alternatively, the ablation probe may further comprise at least one conductor coupled to a contact at the proximal end and further coupled to the electronic indicator to allow the ablation generator to issue a signal to the electronic indicator and thereby control the electronic indicator.

Another illustrative and non-limiting example takes the form of a system comprising an ablation generator having an output circuit adapted for issuing therapy pulses to a port, a controller for controlling the output circuit, and a user interface to allow a user to manipulate the controller, and an ablation probe as in any of the preceding examples, configured for coupling to the port.

Still another illustrative and non-limiting example takes the form of a method of using an ablation probe, the ablation probe being as in any of the preceding examples, the method comprising advancing the probe to a target tissue, and issuing one or more electrical outputs through the probe, while the probe electronic circuit monitors and/or quantifies probe usage.

An illustrative and non-limiting method example takes the form of a method of preparing for a surgery comprising: obtaining a therapy probe, the therapy probe containing a probe electronic circuit; interrogating the therapy probe electronic circuit to determine whether the probe is at end of life (EOL); and either confirming that the probe is not at EOL; or determining that the probe is at EOL and discarding the probe.

Additionally or alternatively the interrogating step is performed via a wireless connection. Additionally or alternatively, the interrogating step is performed by plugging the probe into an ablation pulse generator, and activating the ablation pulse generator to communicate with the probe electronic circuit.

Another illustrative and non-limiting method example takes the form of a method of operation in a therapy probe, the probe including a distal end having one or more electrodes thereon for delivering therapy directed at target tissue, a proximal end having one or more contacts thereon for coupling to the ablation generator, an elongated body between the proximal and distal ends carrying at least one conductor that electrically couples at least one electrode to at least one contact, and a probe electronic circuit in or on the probe and configured to sense usage of the probe, determine a status of the probe relative to a predetermined end of life (EOL) for the probe, and generate an output related to the determined status, the method comprising: the probe electronic circuit sensing usage of the probe; the probe electronic circuit determining that usage of the probe exceeds a predetermined parameter; and the probe electronic circuit generating an indication that probe EOL has been reached.

Additionally or alternatively, the step of generating an indication that probe EOL has been reached comprises generating a visual output on the probe itself. Additionally or alternatively, the step of generating an indication that probe EOL has been reached comprises generating an audible output by the probe itself. Additionally or alternatively, the step of generating an indication that probe EOL has been reached comprises generating a tactile output by the probe itself.

Yet another illustrative and non-limiting method example takes the form of method of operation in a therapy probe, the probe including a distal end having one or more electrodes thereon for delivering therapy directed at target tissue, a proximal end having one or more contacts thereon for coupling to the ablation generator, an elongated body between the proximal and distal ends carrying at least one conductor that electrically couples at least one electrode to at least one contact, and a probe electronic circuit in or on the probe and configured to sense usage of the probe, determine a status of the probe relative to a predetermined end of life (EOL) for the probe, and generate an output related to the determined status, the method comprising: the probe electronic circuit determining, by either usage or age, that the probe has reached EOL; and the probe electronic circuit issuing an electrical output changing a physical appearance of the exterior of the probe in response to EOL.

Additionally or alternatively, the electrical output changing a physical appearance is one that expels ink.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 11 is a flow diagram showing actions in an ablation probe electronic circuit parallel to ablation generator system actions.

DETAILED DESCRIPTION

Figure 1:
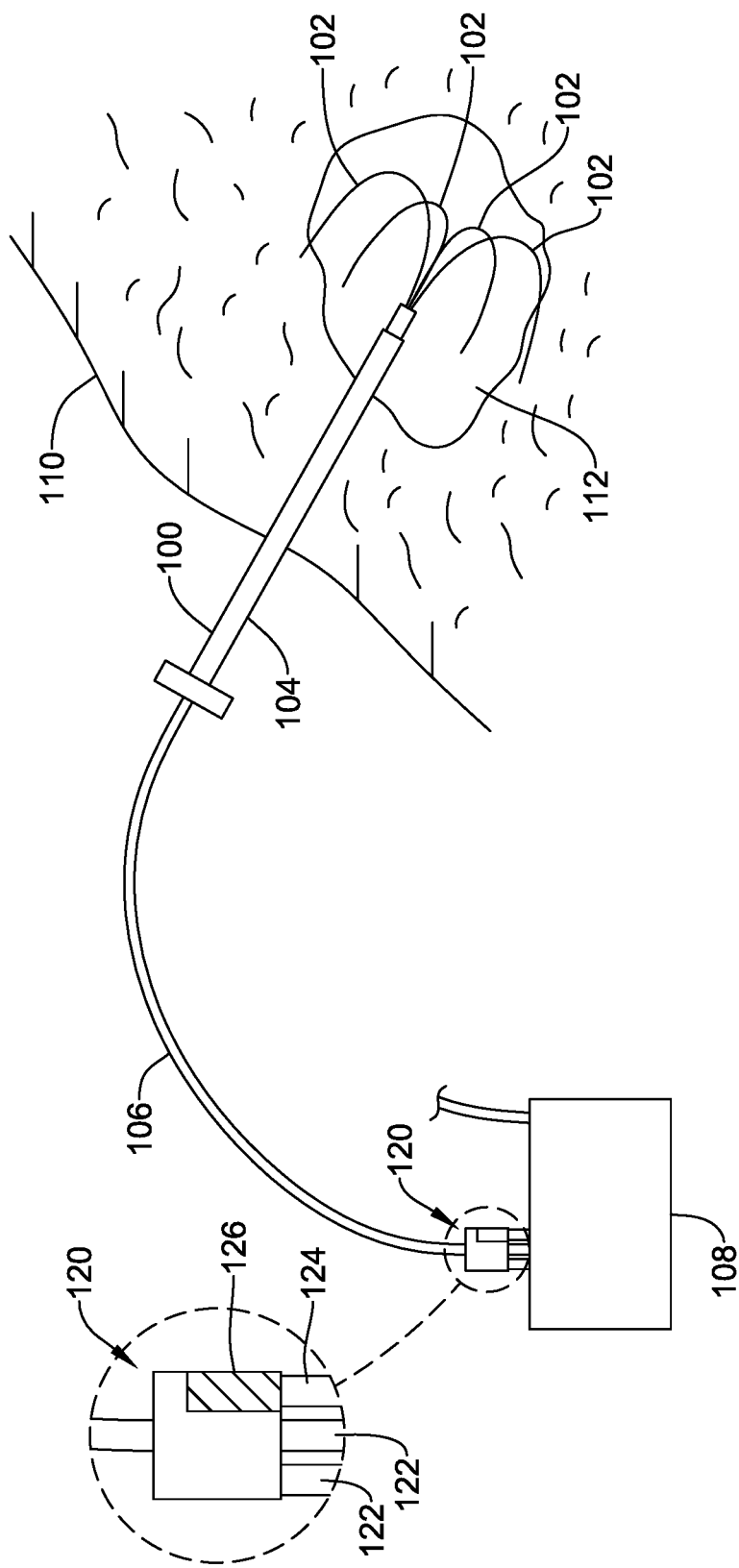
FIG. 1 shows an illustrative ablation system in use on a patient and target tissue.

FIG. 1 shows an illustrative ablation system in use on a patient and target tissue. An ablation probe 100 is shown and includes an elongated shaft 104 that extends to a plurality of tissue piercing electrodes 102 at a distal end thereof. The tissue piercing electrodes 102 can be extended or retracted once a target tissue 112 of a patient 110 is accessed. The proximal end of the apparatus is coupled by an electrical connection 106 to an ablation generator 108. Various features and potential enhancements of such a probe 100 are discussed in U.S. Pat. Nos. 5,855,576 and 6,638,277 as well as US PG Pat. Pub. No. 20190223943, the disclosures of which are incorporated herein by reference.

In the example a manifold 120 is provided to couple the electrical connection 106 to the ablation generator. As shown in the inset, the manifold 120 may comprise a plurality of contact pins 122 that are used to electrically connect to the electrodes 102 of the probe 100, with one or more contact pins 124 connecting to probe electronics 126 within or attached to the manifold 120. In this example, the probe electronics 126 may include, for example, an array of resistors or mechanical switches, a memory, a gate array, or other structure or circuit that can be electrically interrogated and read to determine information about the probe 100. The interrogated information may comprise, for example, a model number for the probe 100 that the ablation generator 108 may use to look up features of the probe, such as the number, configuration and/or properties of the electrodes 102, as well as information such as a use-by-date for the probe. In some examples, the probe electronics 126 may include probe data such as the number and type, size or shape of electrodes 102, as well as stored programs for using the electrodes, such as by storing program data indicating which electrodes to use to deliver ablation, in what order, and/or with what pulse parameters (pulse width, amplitude, relative amplitude, shape, polarity, frequency, etc.). In this way, the probe itself may encode a therapy program to be read by the ablation pulse generator, rather than requiring a physician or user to actually input program parameters.

In some examples, the probe electronics 126 may allow data to be written, as for example, if the probe is used by the ablation generator 108 to issue one or more ablation signals, the probe electronics 126 may comprise a counter and/or memory to allow the fact of use to be recorded, or to allow quantification of use to be recorded. If a user attempts to reuse the probe at a later time, this written information in the probe electronics 126 can indicate the prior use and, if the probe is intended to be a single use device, it may be locked out to prevent further use. In another example, the probe may instead have a defined useful life determined by time since first use and/or a quantity of use, such as a total current, voltage, charge, quantity of pulses, On-Time, power, energy, or other measurable parameter of use, and data written to the probe electronics may indicate the quantity of use or may store other information that allows an ablation generator 108 to determine whether or not the probe 100 can be used or may continue to be used.

In some further examples, below, the manifold 120 may provide a visible or audio indication to the user. For example, when plugged in properly, the manifold may provide a visual or audible cue. Further, the manifold 120 may have a feature to allow the status of the probe, relative to end of life, to be indicated. Such visual indicators may use, for example, a LED or other light to generate a visual output, while audible indicators may use a speaker. For example, and without limitation, for a new probe, a green LED may light up, and for one that has been used, yellow or some other color may light up. In some examples, a permanent marker is provided in a mechanical format. For example, prior to a first use, a visual indicator on the manifold 120 may have a certain color and, after the probe has been used, that visual indicator may be modified by the probe electronics 126 as by, for example, issuing an electrical current that opens or releases a bolus of dye into a visible enclosure. For example, if no dye is seen, the device is ready for use to use; once the dye is seen in the visible enclosure, the device is not to be used. Similarly, if the total quantity of use crosses some threshold, any one, two or all of the electrical, audible, or physical indicators, such as in the dye example, can be used to provide an indication to the user.

It is also contemplated in various examples herein that the probe's use may be disabled automatically when end of life is reached or the probe is otherwise no longer to be used. For example, a fuse may be provided that opens once end of life is reached. Mechanical disablement for single use purposes may be used instead as by, for example, having a spring-loaded portion of the manifold that holds a first, partly retracted position before use and which can be retracted as the manifold is plugged into the ablation generator 108. When the manifold is removed from the ablation generator, the mechanical device extends to a fully extended, locked position that covers the pins 122, 124 and prevents reinsertion of the manifold to an ablation generator 108. Software/firmware-based disabling may use probe memory element that indicates the occurrence of EOL or other condition, which can be read by or communicated to the ablation generator which may issue a lockout preventing use of the ablation probe.

Figure 2:
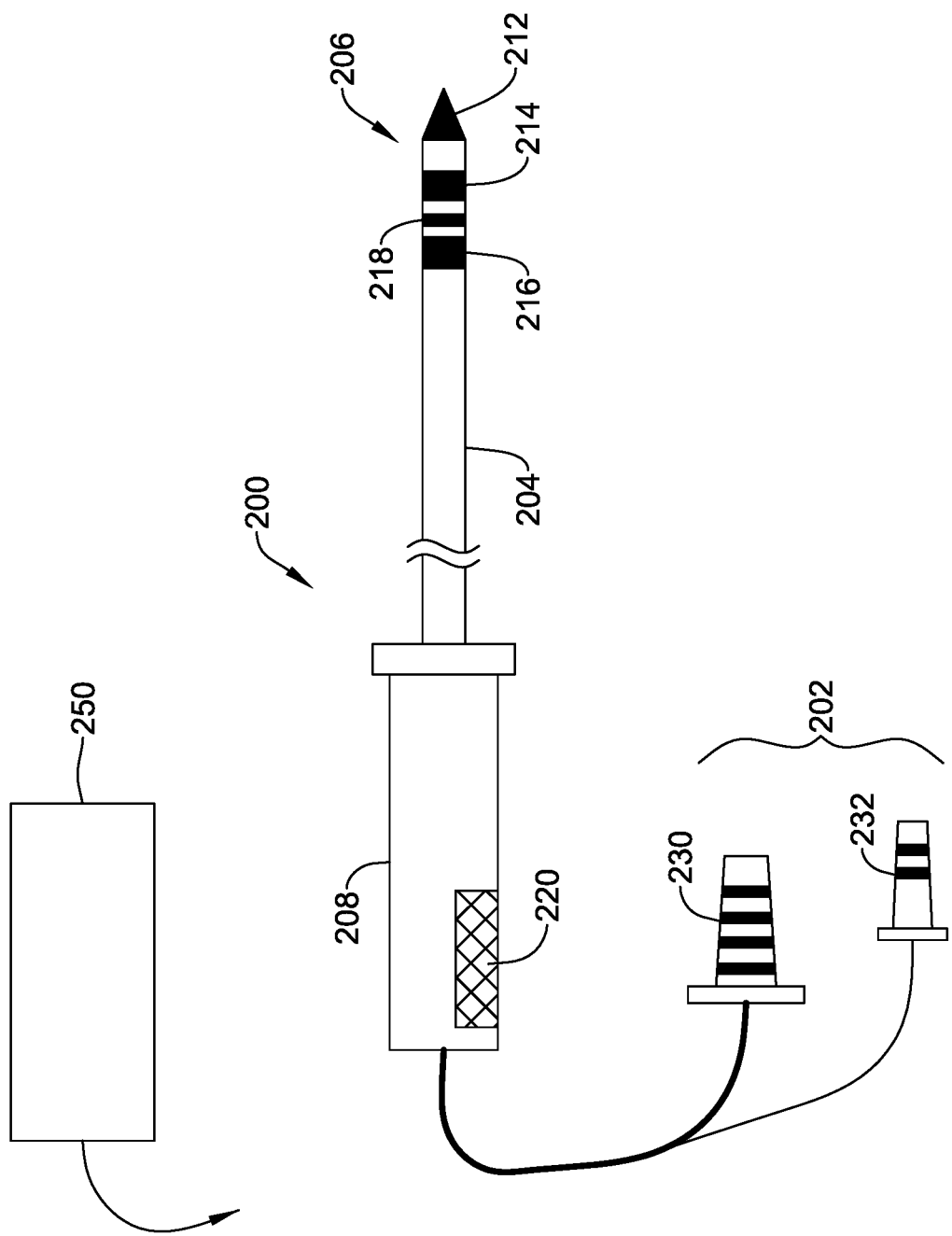
FIGS. 2-3 show illustrative ablation system configurations and details.
Figure 3:
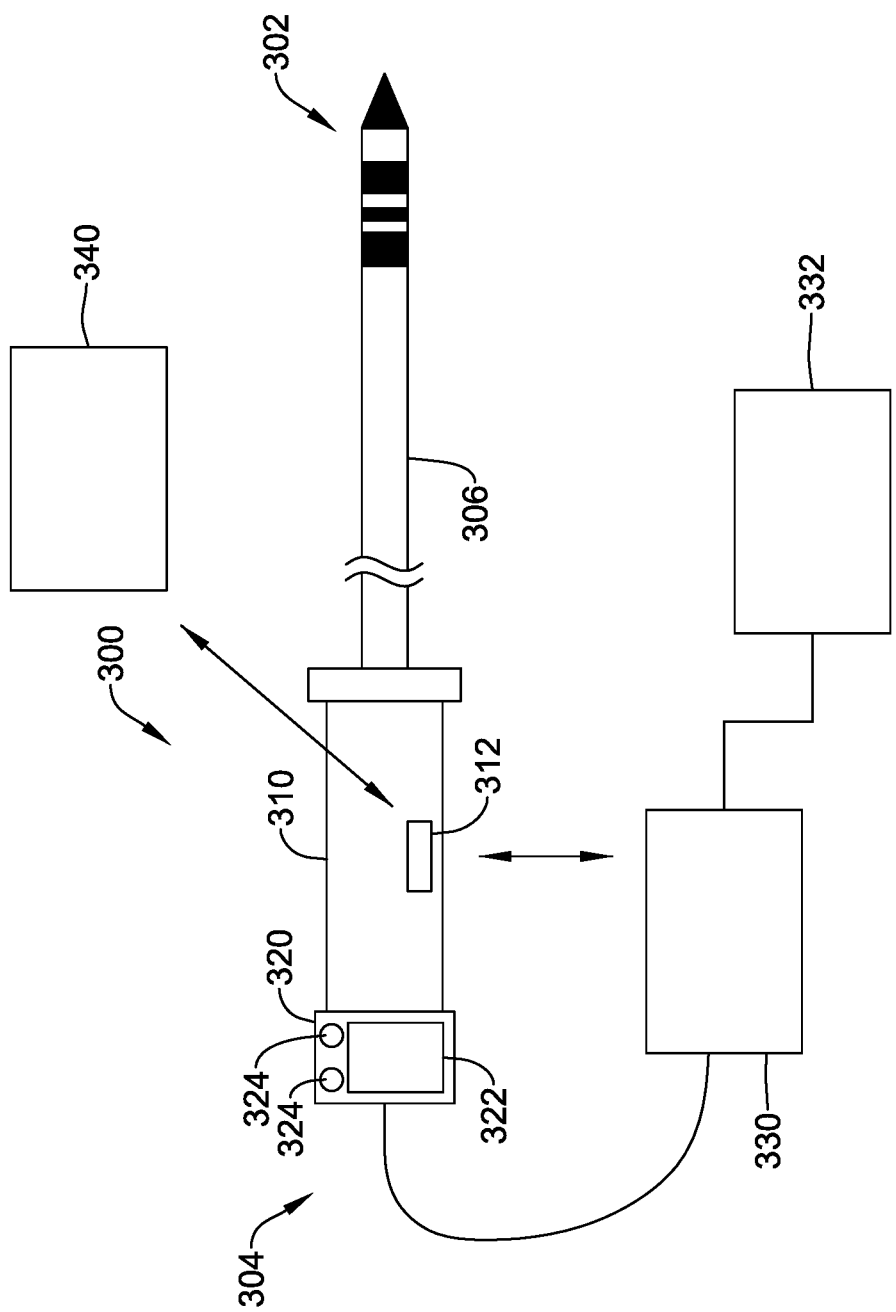

FIGS. 2-3 show illustrative ablation system configurations and details. Starting with FIG. 2, an illustrative ablation probe 200 is shown having a proximal end 202, an elongated body 204, and a distal end 206. The distal end 206 includes one or more electrodes 212, 214, 216, 218 that may be used for therapeutic and/or diagnostic purposes, such as to deliver therapy energy, for example, electrical pulses or other signals, to target tissue in various combinations. The electrodes may be moveable or adjustable, such as by placing one or more on an expandable element (such as an inflatable balloon) or by providing a sheath moveable over an electrode to reduce or increase its exposed surface area, as discussed in US PG Pat. Pub. No. 20190223943, the disclosure of which is incorporated herein by reference.

A bipolar therapy mode may use, for example, a first electrode such as electrode 216 as an anode and a second electrode such as electrode 212 as a cathode for one or more phases of therapy output. Bipolar therapy may also be achieved by having two probes of similar or different design both placed in or near the target tissue. Monopolar therapy implies the use of a remote return electrode such at a patch 250 that would typically be placed at a distant and innocuous position on the patient's skin. Therapy output can take any desired form, including the use of sinusoidal outputs or pulsed outputs such as square (or other shape) waves, and may range from low to high frequencies well known to those skilled in the art.

Inactive electrodes may be used during therapy, if desired, to monitor electrical fields that result from activation of therapy electrodes, thereby providing information to the ablation system relating to the status of patient tissue, such as indicating how the impedance of tissue is changing. In the illustration shown, one of the electrodes 218 has a smaller surface area than other electrodes and may serve as a sensing electrode only, if desired; in other examples, any electrode may be used for therapy output, and electrodes may be ganged together in common for therapy purposes if desired. Additional features, such as a temperature sensor, optical detector, pressure sensor, microphone, or force sensor may be provided on the elongated shaft 204 and used for various reasons, such as to monitor or provide feedback on the insertion process, probe position, target tissue characteristics, progress of and conditions during surgery/ablation, for example.

The proximal end 202 is shown having two plugs 230, 232. One plug 230 may couple to therapy output port(s) of an ablation generator and can be configured to receive high power signals if desired, while the other plug 232 can be attached to an ablation generator or to a separate monitoring device, if desired, and is used to power and interact with the probe electronic circuit 220. While custom plugs 230, 232 are shown, any shape or design, including standard formats, may be used for one or the other 230, 232, such as, for example and without limitation, using a USB or Micro-USB format (or other standard) for plug 232. A single plug may be used instead.

Further in the example shown in FIG. 2, the elongated shaft 204 may include a handle 208 secured on one end, with the handle designed to allow a using physician ready control of the device. In the example shown, a probe electronic circuit 220 is provided in association with the handle 208. Uses for the probe electronic circuit 220 are described in detail below and may include, for example and without limitation, monitoring and/or sensing probe usage, determining a status of the probe relative to a predetermined end of life for the probe, and generating an output related to the predetermined status. The probe electronic circuit 220 can be coupled to sensors on the probe, including those at or near the distal end, and can also be electrically coupled (directly or by field sensing) to the conductors through the probe that couple the proximal end to the electrodes. The output of the probe electronic circuit 220 may be provided to the ablation generator or to a separate monitor via plug 232. In some examples shown below, the output can be generated to provide a visual and/or audible output on the probe 200 itself.

FIG. 3 shows another example. Here an ablation probe 300 has a distal end 302 shown as carrying one or more electrodes, a proximal end 304, and an elongated shaft 306 therebetween. A handle 310 is shown on and/or attached to the elongated shaft 306 and has therein a probe electronic circuit illustratively shown at 312. The probe electronic circuit 312 need not be limited to any particular position or orientation. Also along with the handle is one a set of visual indicators 320. The visual indicators 320 may include, for example, and without limitation, electronic lights, such as LED-type lights as shown at 324, or a screen 322, which may be an LCD or LED screen, for example, each of which are forms of electronic indicators (as is a speaker, though a speaker would provide visual, rather than audible feedback). One or more of the visual indicators may instead be mechanical in nature, such as by having an enclosure coupled to a dye reservoir; when some condition takes place, such as end-of-life of the probe 300, the dye can be expelled into the enclosure and becomes visible.

In another configuration, the electronic circuit 312 may couple to a tactile feedback device, such as an imbalanced rotor, that may be used to generate a shaking or vibrating sensation in the handle 310 to indicate a condition requiring further attention of the user. For example, if a force sensor is at or near the distal end 302 of the probe 300, the electronic circuit may interpret a signal from the force sensor as indicating impact with a solid object (in surgery, this may be, for example, a bone) or some other impediment (such as a fascial layer or other tissue transition), and generate the vibration to alert the user to confirm positioning before advancing further. In another example, a strain sensor may be embedded in the elongate shaft 306 to indicate whether the shaft 306 is starting to bend or curve, again used to generate a vibration and tactile feedback. In still another example, a tissue condition near the distal end 302 may be sensed, such as temperature, pH, or an optical condition. In an example, an optical sensor may be provided near the distal end and a target tissue or a tissue to be avoided may be marked with a dye, for example, with tactile feedback provided to allow the user to know when the optical sensor detects proximity with the tissue that has the dye.

In this illustrative example, the proximal end 304 of the ablation probe is coupled to a signal generator 330 which, in turn, has a user interface as shown at 332 which may be or may include, for example, a touchscreen or monitor. The electronic indicator(s) on the ablation probe 300 are thus separate from the touchscreen or monitor 332 of the signal generator 330.

Also in this illustrative example, the probe electronic circuit 312 may optionally include a wireless communication functionality, such as by having an antenna and associated driver circuitry (such as a Medradio or Bluetooth antenna/circuit) to wirelessly communicate with the ablation generator 330 or another monitoring system 340 in the vicinity. In an illustrative example, and as shown below, the probe electronic circuit 312 may be configured to harvest energy for its own use from therapy outputs generated by the ablation generator 330, and may provide feedback to the user independent of any functionality of the ablation generator 330. As a result, the ablation generator 330 can be a common, commercially available ablation signal generator, while the specialized feedback functions provided by the probe 300 can be provided without requiring an established technology base in the field. The probe itself may have an interface (screen, lights, etc.) to allow the user to access the added functionality. If desired, a separate monitoring apparatus 340, which can take the form of, for example and without limitation, a smartphone, a tablet, a personal digital assistant, or a dedicated device, may be used to aid in the ablation procedure by communicating with the probe in ways that the standard commercial ablation generator may not be capable of.

Figure 4:
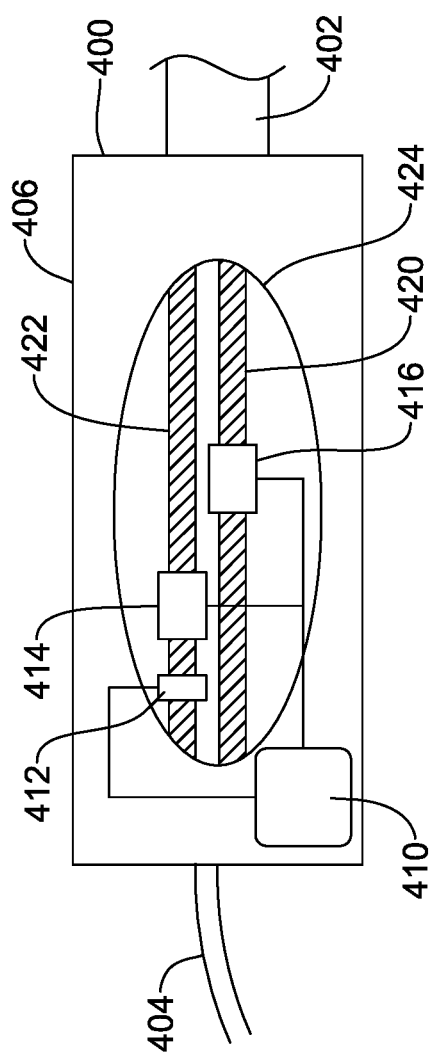
FIGS. 4-5 show partial cut-away views of illustrative ablation probes.
Figure 5:
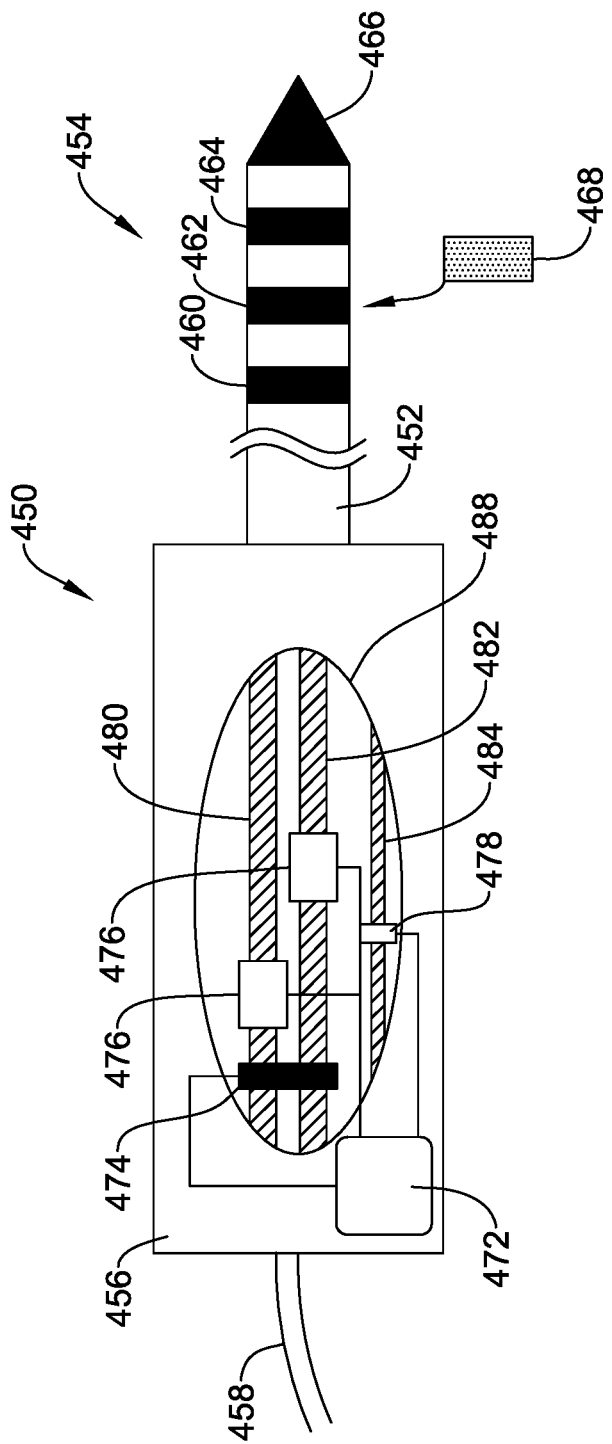

FIGS. 4-5 show partial cut-away views of illustrative ablation probes. Starting in FIG. 4, a proximal portion 400 of an ablation probe is shown, with a cutout region at 424 showing, at least in sketched form, an interior having first and second conductors 420, 422 that are configured for electrically coupling electrodes at the distal end of the probe with the proximal conductor 404 that couples in turn to an ablation generator. A probe electronic circuit 410 is coupled to the first and second conductors 420, 422 in at least one of the following ways.

In some examples, an energy harvesting circuit 412 may be provided to couple to one or both of the conductors 420, 422. In an example, an inductive link may be formed at 412 so that when current passes through a conductor 422, current will be generated in element 412 to provide power to the probe electronic circuit 410. In another example, a direct electrical connection is made, with appropriate isolation circuitry included (such as, for example and without limitation, a rectifier in line with a capacitor and voltage regulator) to avoid allowing large voltage to reach the probe electronic circuit while siphoning current off into a power supply capacitor. The capacitor may store power at least temporarily for use by the probe electronic circuit 410. An isolation switch may be provided so that once the capacitor reaches a desired stored voltage, the isolation switch opens to decouple the conductor 422 from the probe electronic circuit 410. While only a single coupling is shown at 412, the probe electronic circuit may couple to more than one line passing through the probe, and, if desired, also to a system ground or reference line that may be provided as well. Other configurations for capturing and storing power at low voltage levels from a high voltage line may be used, as are known to the skilled person. Data may be conducted through the therapy lines as well, using, for example, technology similar to that used for broadband-over-power-line systems, in either 1-way or 2-way manner. In other examples, dedicated power and/or data lines may be provided separate from the therapy conductors, such as illustrated by FIG. 2.

Also in some examples, the conductors 420, 422 may be coupled to current sensors shown at 414, 416, to allow sensing of currents passing therethrough. Further, the sensors at 414, 416 may also, or instead, sense voltage in each conductor 420, 422. By sensing voltage and current, the probe electronic circuit 410 may be able to determine characteristics, such as impedance, encountered during therapy while reducing the influence of connector and line losses that can occur at the interface/coupling of the probe to the ablation generator. In another example, sensed voltage may be communicated, by wire or wirelessly, to the ablation generator for comparison to the voltage provided by the ablation generator, allowing line and coupling losses to be determined.

FIG. 5 shows another example. An ablation probe is shown at 450, having an elongated shaft 452 coupling a distal end 454 to a proximal end 456, with a proximal cable 458 extending to an ablation generator (not shown). The distal end 454 includes a plurality of electrodes 460, 462, 464, 466. Optionally in this example, one or more of the electrodes 460, 462, 464, 466 may be provided with a coating 468. In some examples, such a coating 468 is used on all electrodes. The coating 468 may be permanent in some examples, and may take any form known in the art, from using expanded carbon, to titanium nitride or iridium oxide, or any other coating as desired.

In one example, the coating 468 is dissolvable and may be used to aid in various diagnostic processes. For example, the coating 468 may be an organic and non-toxic coating, such as a sugar coating, that will dissolve over the course of several minutes, up to one or two hours. In an example, coating 468 provides a measure of how long the device has been positioned in the body. As the coating 468 dissolves, the electrode on which it is placed remains clean of any attached body fluid or film, which may form on other, non-coated electrodes, causing the electrode on which the coating 468 is provided to have a predictable impedance curve over time, allowing comparison to an impedance trend over time observable with other electrodes.

In another example, a four-wire measurement routine can be used to eliminate probe information from the impedance measurement. A four-wire measurement method may use separate pairs of current-carrying and voltage-sensing electrodes to make more accurate measurements than the simpler and more usual two-terminal sensing. Thus the induced electrical field in the non-current carrying electrodes can be measured, providing additional information, instead of or in addition to impedance measured using the current carrying electrodes themselves.

In another example, therapy delivery can take place using two electrodes (such as electrodes 462, 466) and two other electrodes (electrodes 460, 464) are not used for therapy delivery; it may then be expected that an impedance measurement taken using the therapy electrode pair would reflect the formation of a film, oxidation, or other electrode interface change caused by therapy outputs, while the impedance measurement using non-therapy electrodes would not. In this example, measurement pulses may be applied between therapy pulses. For example, therapy pulses may be issued by the ablation generator, transmitted through coupling wire 458 to conductors 480, 482 and thence to electrodes at the distal end 454 of the ablation probe. Measurement pulses may also be generated by the ablation generator, or may instead be generated by the probe electronic circuit 472, which may have its own power source (such as a battery), which may use power harvested from the conductors 480, 482 during therapy outputs, or which may be separately powered by the ablation generator or another device (such as in the configuration of FIG. 2). Data may be conducted through the therapy lines as well, using, for example, technology similar to that used for broadband-over-power-line systems, in either 1-way or 2-way manner, to allow communication between the ablation generator and the probe electronic circuit 472.

In some examples, frequency scanning can be used to obtain an impedance spectrum, if desired. Such an approach may adjust frequency of a delivered test signal across a plurality of frequencies to characterize both real and reactive or imaginary components of the impedance and/or to identify poles, zeros and/or inflection points in the frequency response of the system and/or tissue. Particular frequencies that appear to reflect resonance of the circuit may be noted. To use such an approach to track therapy progress, a pre-therapy scan may be done across several frequencies (3 to 10 frequencies, for example, or more or less, as desired), and the scan may be repeated from time to time during a therapy regimen.

In some examples, changes to the impedance may be tracked and used to estimate therapy progress. For example, when cell membranes become incompetent, fluid inside the cell membrane escapes, which typically results in lowering the impedance of surrounding, extracellular fluid. In another example, intact cells may be understood or modeled as small capacitors, to a certain extent, and therefore as those cells are destroyed, the reactive impedance in the tissue will change to reflect lower capacitance. In other examples, tissue may be modeled as having a quasi-resonant frequency, and the pulse width of applied pulses can be modified so that the characteristic frequency (or a harmonic thereof) of applied square waves matches or is close to the tissue quasi-resonant frequency. If a non-square wave is used, then, for example, a sinusoid therapy signal may be modified to change the frequency thereof, again, to match or be closer to the quasi-resonant frequency. In other examples, mismatch of the applied signal may be the goal, and the applied therapy signal may be manipulated to avoid the quasi-resonant frequency of the tissue.

Any of these, or other, impedance or tissue characterizing methods may be implemented using the embodiments shown herein. In some examples, the probe electronic circuit 472 may be used to generate test signals and record responses thereto. Additionally or alternatively, the probe electronic circuit may be used to monitor responses to applied therapy signals or test signal from the ablation generator (not shown in FIG. 5).

In some examples, a separate line 484 in the ablation probe may be coupled, as indicated at 478, to the probe electronic circuit 472, without continuing to the proximal cable 458 that plugs into the ablation generator. In other examples, the separate lines 484 may continue into the proximal cable 458 to the ablation generator. Multiple lines similar to 484 may be provided. The separate line 484 may be an electrical conductor, or it may be an optical conductor, such as an optical fiber, as desired.

An optical conductor at 484 may be used to optically interrogate and retrieve information from the tissue at or near the distal end 466 by providing a lens, if desired, at or near the distal end 466. As tissue is ablated, the optical conductor may be used to observe tissue changes. In another example, the optical conductor can be used to observe flexing of the shaft 452, as by enclosing the distal end of the conductor with a reflective end; when the optical conductor is flexed along with the shaft 452, the properties of light reflected within the optical conductor will change, allowing flexion of the shaft 452 to be monitored. In still another example, the optical conductor can be used to observe tissue as the probe is advanced, to ensure a target tissue is reached without impinging on non-target tissue.

An electrical conductor or conductors at 484 may couple to one or more electrodes 460, 462, 464, 466, and may be used to issue and receive impedance test signals, or to receive electrical field measurements during therapy, if desired. An electrical conductor at 484 may instead or additionally couple to a temperature sensor such as a thermocouple or thermoresistor, and/or to a chemical sensor or acoustic sensor to sense conditions (temperature, pH, other chemicals, and/or sounds) at, in, or near the target tissue proximal to the distal end of the probe. A motion sensor may also be used to, for example, detect movement of the probe distal end as it is advanced into tissue or during use. A motion sensor, for example, may be used to detect deflection of the distal end of the probe during therapy which, in some circumstances, would be undesired, and may be used to generate an error signal causing interruption of therapy.

Figure 6:
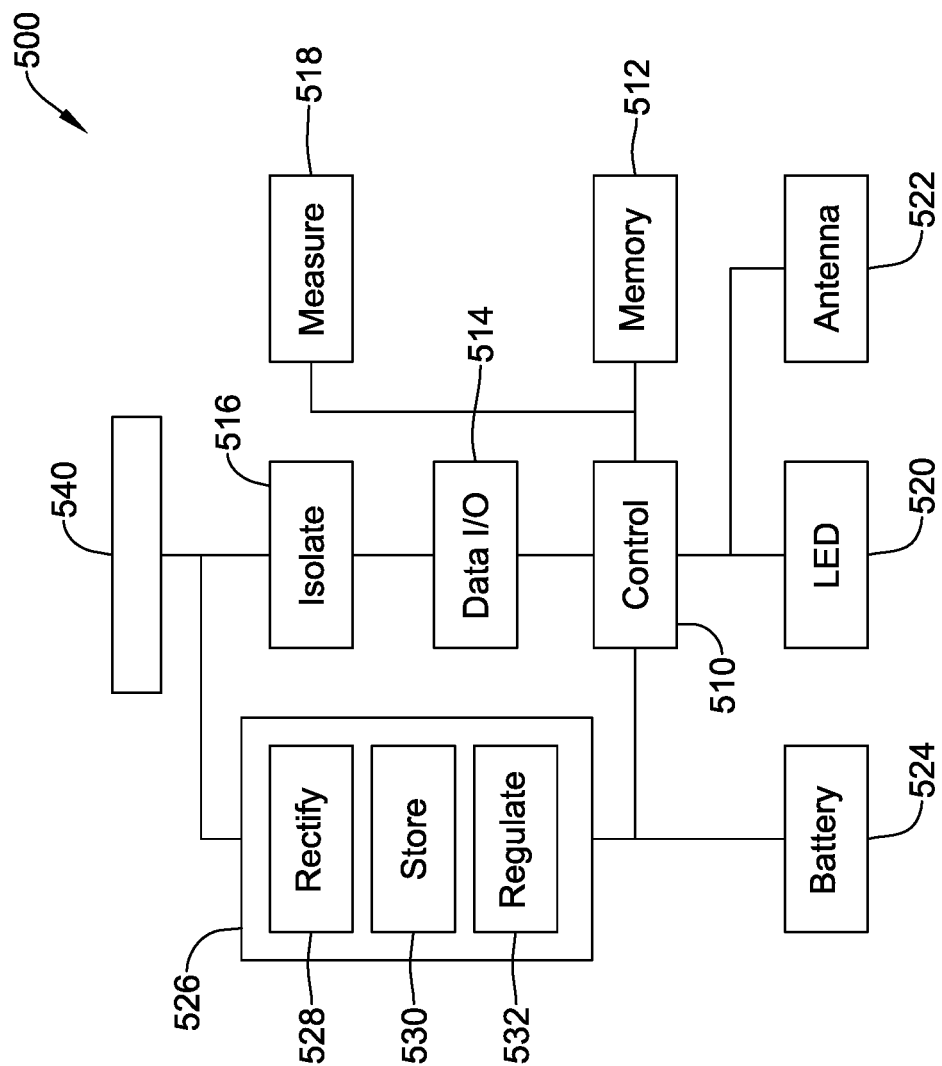
FIGS. 6-7 are functional block diagrams for illustrative probe electronics.
Figure 7:
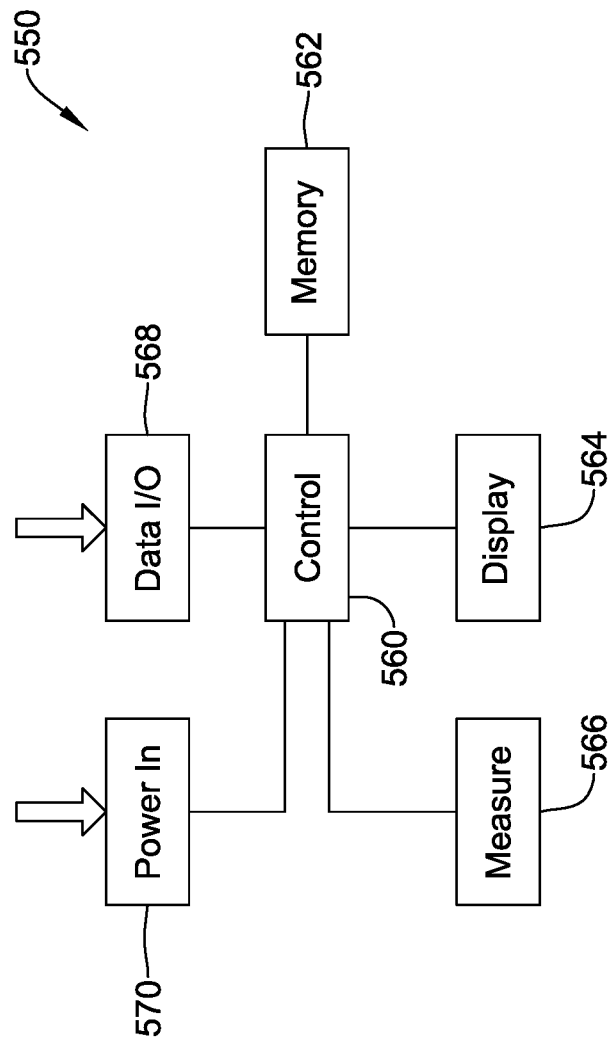

FIGS. 6-7 are functional block diagrams for illustrative probe electronics. Starting with FIG. 6, an illustrative circuit 500 may include a control module 510, which may take the form of an application specific integrated circuit (ASIC) alone, a microcontroller alone, or a combination thereof. In another example, the control module 510 may be a field programmable gate array or other logic circuit. The complexity of operations for the circuit 500 may determine how complex the control module 510 needs to be for a certain implementation. In the illustration in FIG. 6, a relatively sophisticated approach is shown.

As noted, simpler versions may be used. For example, a system may include a gate array that can be configured to receive a signal from the conductor 540, determine based on a pattern in the received signal that an interrogation signal has been received, and respond with an identifying signal. For such an example, much of the circuitry shown would be eliminated.

Another example would use an RF ID tag, allowing the identity (Model number, possibly plus the serial number and/or a use by date) of the probe to be obtained. Using an RF ID tag approach, a further example may include a circuit that, when interrogated, provides a responsive signal encoding data, in which the responsive signal encodes data relating to the usage of the device. For example, the RF ID circuit may encode a two-part message, with a first part indicating a device identifier, and a second part encoding re-writable data related to any of the usage related parameters noted above and below. In still another example, the two-part message may include a device identifier and an indication of end of life (EOL) status, rather than a parameter. In still another example the RF ID output may be designed to overwrite identifying information at EOL, so that a one-part message is generated either indicating the device identifier (Model and/or Serial number), or an EOL message.

Turning back to FIG. 6, the control module 510 may couple to a memory 512, which can store operating instructions and data and which may also be used to store measurement data as it is taken, if desired. The memory 512 may be any suitable type, including any of RAM, ROM, and Flash memory, for example. The control module is coupled via a data I/O block 514 to an isolation block 516 which in turn may couple to a conductor 540 of the probe. Alternatively, the isolation block 516 may be omitted, and a dedicated line for communication may be provided in place of the conductor 540. The data I/O block can be used to store a data queue as it is received and/or to block issue data outputs, using known methods and circuitry (i.e., registers and pointers coupled to an amplifier that generates output square waves or other waves, or to a modulator/demodulator). The control block 510 may also couple to a measurement circuit 518. The measurement circuit 518 may be configured as a driver or other pertinent circuitry to allow measurements to be taken, including current, voltage, impedance, temperature, chemical, acoustic, motion, etc., as noted previously.

Power for the device may come from a dedicated connection (see, for example, FIG. 2). In some examples, power may be provided by a battery 524. In other examples, power may be provided by a power harvesting circuit 526, which may include a rectifier 528, a storage block 530 (such as a capacitor), and a regulator 532 that can be, for example, a standard power regulator to provide, for example, a 1.8 or 3.2 volt supply to the control circuit 510. Multiple power regulators may be provided to allow different functions to be performed at different power levels, if desired; for example, the measurement circuit 518 may use a different power supply than the control circuit 510. More than one power sources may be provided and used in some examples, while other examples will only use one of the several sources described. For example, a battery power supply 524 can be used to monitor probe status prior to use, and once the probe is in use, harvested power from block 526 may be used.

Output sub-circuits for annunciating information may be provided as well including, for example, an LED 520 which can provide visual signaling. Rather than or in addition to an LED 520, a screen may be provided, and/or an audible alert system may be used in which case a speaker may be provided. As noted, a tactile output can be provided by providing a vibrating element. In the example, an antenna is provided at 522 for use in transmitting data wirelessly to other devices, as previously described.

FIG. 7 shows another example circuit. A control module 560 is provided and may be similar to that described above for the control module 510 described with reference to FIG. 6. A memory 562 is also shown, and is again similar to that of FIG. 6. In this example, dedicated power and communication lines are provided in the probe and couple to a power-in sub-circuit 570, which may include, for example, a capacitor and regulator, if desired, or which may directly couple instead to the control block 560. The use of a capacitor and regulator is optional, but may be considered to prevent power surging during use of the ablation probe from affecting circuit operation. Measurement circuitry 566 is shown as well, and may be similar to that described relative to FIG. 6. A display 564 may take the form of, for example and without limitation, an LCD or LED screen, or other suitable display.

Figure 8:
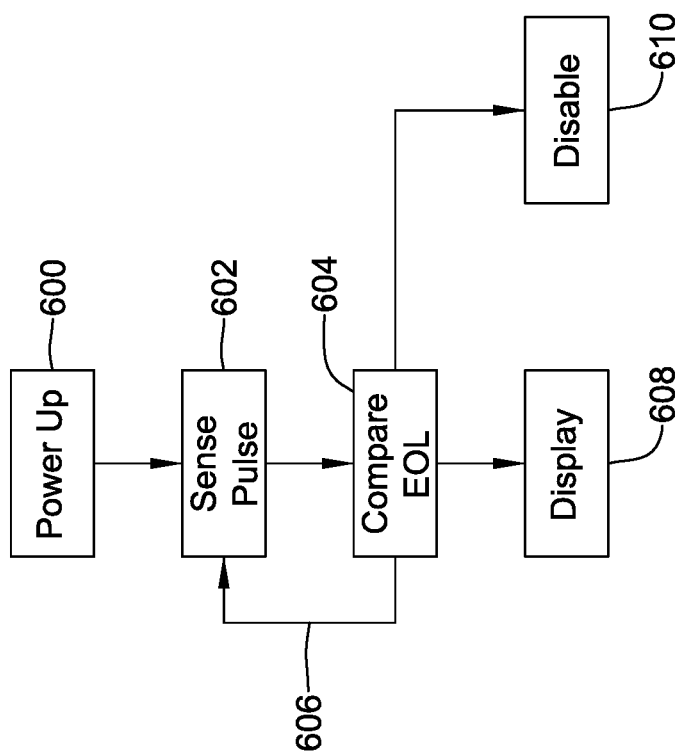
FIGS. 8-10 show, in block form, illustrative methods.
Figure 9:
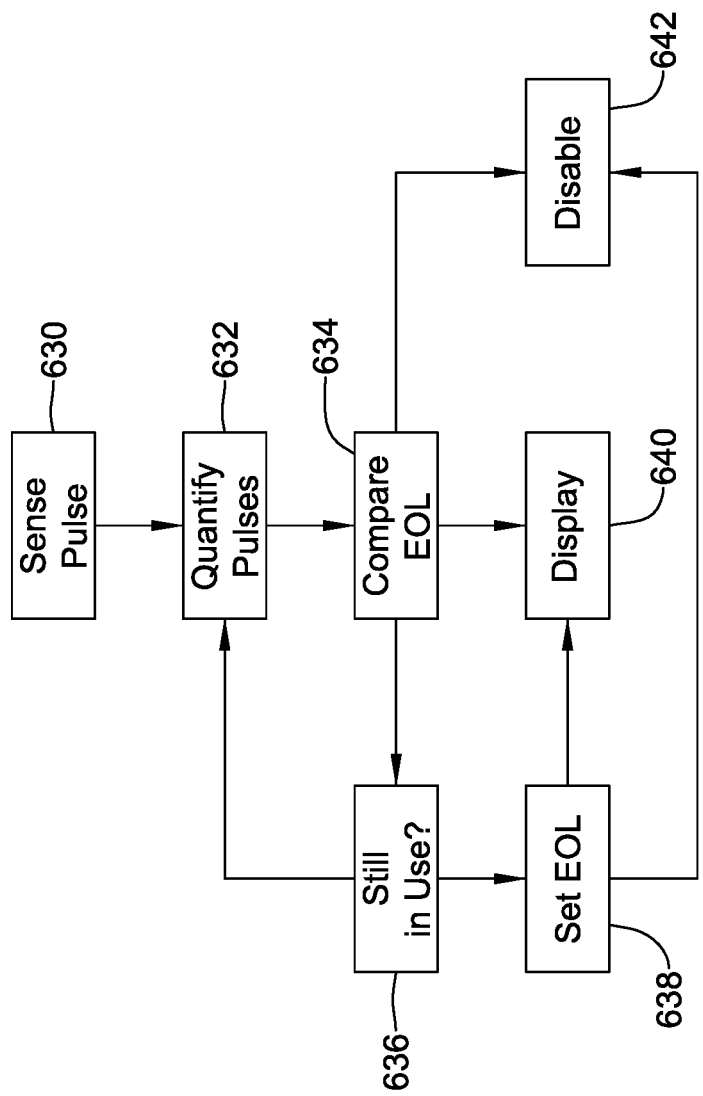
Figure 10:
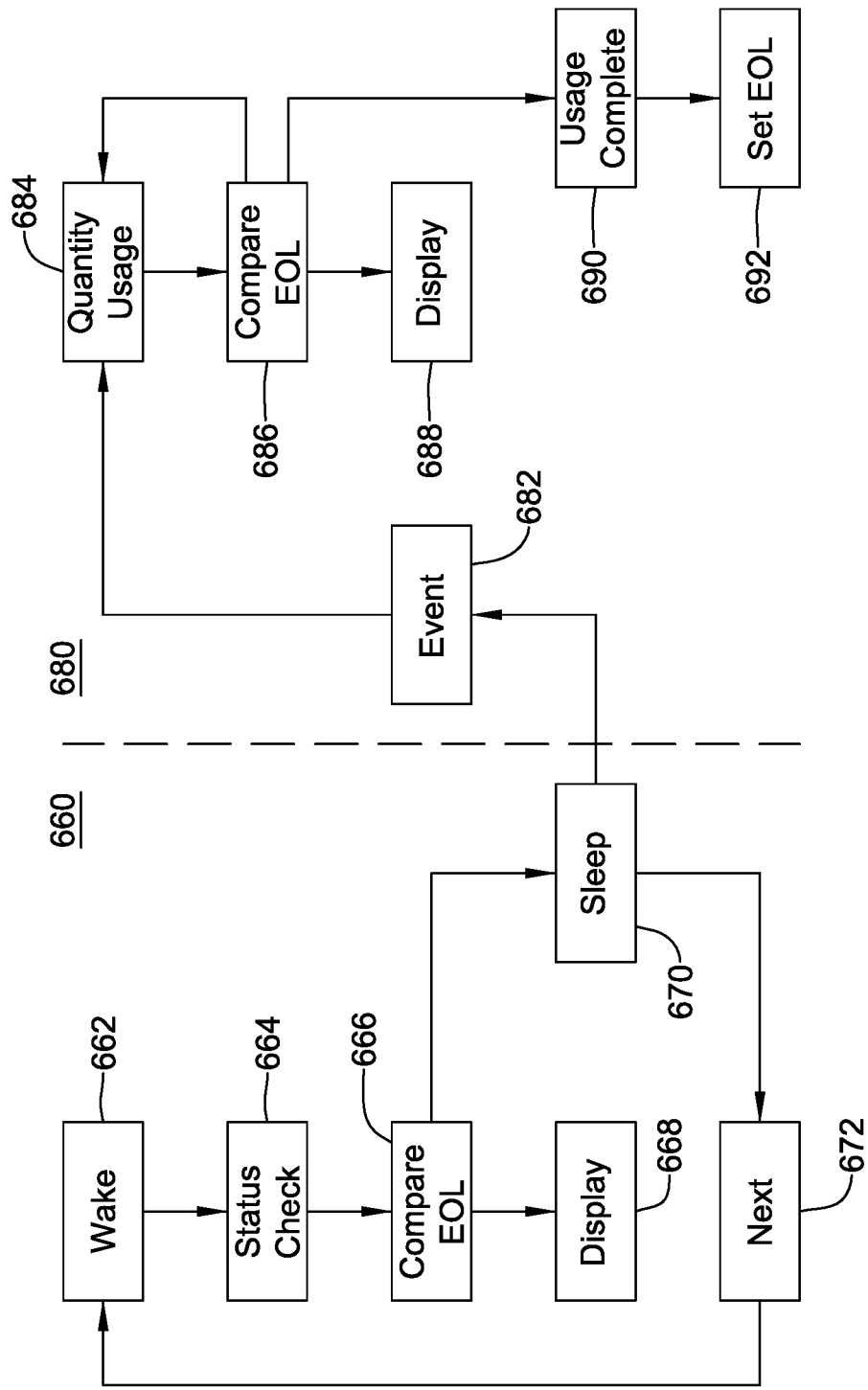

FIGS. 8-10 show, in block form, illustrative methods. Starting with FIG. 8, a power-up 600 starts the method. In an example, power-up may occur when the ablation probe is plugged into an ablation generator, and the ablation generator may be configured to provide dedicated outputs for use by the probe circuit. In another example, power-up may occur after the ablation probe is plugged into the ablation generator, when signals are issued to the ablation probe and carried by conductors therein to the distal end of the probe; as such signals are issued, the probe electronic circuit harvests power that is transmitted and powers itself on. Within a few pulses of therapy initiation, the probe electronic circuit will come on-line and begins to track probe usage by sensing pulses, as indicated at 602. With new pulses, the probe electronic circuit calculates a usage metric, such as the quantity of delivered charge or current, the amount of delivered power, the number of pulses delivered, the total on-time, time since therapy began, or other characteristic. As usage takes place, the probe electronic circuit compares to metrics for end of life, which may match whichever usage metric is in place. In an example, a maximum utilization of one or more electrical interfaces (electrodes) can be monitored and used, where utilization is measured in terms of delivered charge, power, total active time, etc. If EOL is not yet reached, the method reverts as indicated at 606 to await a next pulse in block 602. Once EOL is reached, a display or other annunciation of EOL is triggered, as indicated at 608. In block 608, a visual, audible, or tactile output may be generated on the probe itself. EOL can be indicated actively using lights/screen and/or audible and tactile output, as well as by providing an irreversible passive marker, such as by expelling an ink marker into a visible container. In other examples, block 608 may be performed by generating an output alert via the ablation generator, or via a separate device (such as a tablet, smartphone, PDA, etc.) to alert the user of EOL. In some examples, EOL may be indicated in stages, such as a first alert indicating EOL is approaching, a second alert indicating EOL has been reached, and a third alert indicating usage beyond EOL, for example. Optionally, as indicated at 610, EOL may be accompanied by the probe being disabled.

FIG. 9 shows another example method in block form. Here, the power-up element is omitted, as may occur if the probe has its own energy source such as a battery. Power up may be included, optionally. At block 630, the method begins with sensing a pulse. Pulses are then quantified, as indicated at 632. As noted previously, quantifying here may mean the total number of pulses, the number of pulses for a given electrode, the amount of current or power delivered (overall or for each electrode), total duration of use, total on-time, or other measurable. The method continued by comparing the quantity of uses to an EOL metric, as indicated at 634. If EOL is reached, the method proceeds to one or both of blocks 640 to display or otherwise annunciate EOL (or approaching EOL) and/or block 642 to disable the probe by, for example, opening a switch or fuse, or storing an EOL status to be read by an ablation generator. The example of FIG. 9, if EOL is not yet reached at 634, next determines if the probe is still in use, as indicated by continued receipt of pulses, for example, or by determining using a temperature sensor that the probe remains at least partly inserted into patient tissue, as indicated at 636. If the probe is still in use, pulse quantification continues at 632. If the probe is found to be no longer in use, such as by passage of time since the last pulse was observed, or by detecting withdrawal from the patient for a prolonged period of time, the probe electronic circuit sets EOL as indicated at 638 and proceeds to one or both of blocks 640, 642. By configuring the probe to activate block 638, the probe itself can ensure it is a single use device. In other examples, such deactivation may be prevented until the surgical procedure is over, such as may be indicated by removal of the probe from the patient and/or from the ablation generator, to avoid possibly interfering with completion of a procedure. In an example, EOL at 634 triggers only display or other annunciation, while the operation at 638 triggers disabling the probe via block 642 as well as the display at 640.

FIG. 10 shows another illustrative method. A pre-use state is shown on the left side, at 660, and a use state is shown on the right side at 680. The pre-use state can be the state of the probe after it leaves manufacturing and before it is used. While the probe is awaiting use, the probe electronic circuit, operating under battery power, can periodically wakeup, for example according to a timer, as noted at 662. The probe will then perform a status check at 664 which may be as simple as checking a time since manufacturing and comparing to time-based end of life in some examples, as indicated at 666. The status check 664 may also check other factors, such as device integrity, which may be an electrical continuity check in some examples, and/or a device temperature history (determined by monitoring of temperature with a temperature sensor), device drop (determined by use of an accelerometer to ensure the device is not dropped and possibly damaged), etc. Any failure to stay within predetermined bounds for such factors may be deemed an error triggering an error which may be treated similar to EOL.

If EOL, or other error, is identified, this may trigger a display 668 of the EOL or error status, such as activation or deactivation of a visual signal, such as an LED or an externally visible dye marker. Otherwise, the device can return to a sleep state at 670, until a next iteration 672.

When an event is identified at 682, the device transitions to the use state. An event may be, for example, plugging in the probe to an ablation generator, or the issuance of a therapy or other pulse from an ablation generator. In the use state, the probe electronics are configured to quantify device usage 684. As the device is used, the amount of usage is compared to an EOL usage level at 686. If EOL is reached, a display 688 of the EOL state is triggered. Here, because the device is being used, the EOL display at 688 may use a screen, lights, audible, or tactile approach, or a combination of more than one of these modes, to annunciate that EOL is approaching or has been reached. The display 688 may include a display on the ablation generator, or on the probe itself, or on a separate monitoring apparatus, if desired. When the use concludes, the probe electronics may determine that usage is complete 690, and the EOL is set and displayed as indicated at 692 in fashion similar to that of block 668. Usage complete may be determined at 690 by observing, for example, disconnection from the ablation generator by a change in electrical connection, or by change in temperature.

FIG. 11 is a flow diagram showing actions in an ablation probe electronic circuit parallel to ablation generator system actions. On the left side at 700 are actions performed with the ablation system, for example, by the actions of a physician. On the right side at 720 are actions taken by the probe electronic circuit. At the start of a procedure, the probe is connected to the ablation generator, as indicated at 702. In response, the probe electronic circuit can power up, as indicated at 730; by power up, this may mean transitioning from a sleep state to an active, use state for example with a device having a battery 732. In other examples, the power up at 730 may occur because the connection made at 702 brings power to the probe electronics by a dedicated connection 734 (if no battery is included in the probe electronics). In still other examples, power may be harvested when therapy pulses start being delivered; if so, the probe electronics may not be used until block 706 of the system usage is reached.

Following power up at 730, the probe insertion performed at 704 may be aided by the probe electronics to guide insertion as indicated at 740. For example, the probe electronics may use any of several available sensing characteristics, depending on configuration, to guide insertion 740. For example, a force sensor, a sensor to detect bending of the probe shaft, impedance (Z), an optical detector, and/or a chemical sensor, each of which is indicated at 742. Feedback may be provided by the probe electronics in any of several ways, including tactile, sound, or visible indications, as indicated at 744.

Next, with the probe placed as desired, therapy starts as indicated at 706. The probe electronics can be used to monitor therapy delivery as indicated at 750. Monitoring can include monitoring characteristics related to the interface, electrical field propagation, impedance, movement, sound, visible features, chemical changes, and/or temperature sensing, as indicated at 752. In addition to these features, usage may be monitored as indicated in FIGS. 8-10, for example, to track toward end of life. If the monitoring reveals a change in sensed characteristics, or an error, this can be annunciated by visual, tactile or audible feedback to the user, as indicated at 754. If a fault or EOL is detected, this may trigger disabling of the probe in some examples, either with the probe itself becoming disabled or by storing the EOL status in the probe to be read by an ablation generator.

When the therapy regimen is completed, as indicated at 708, the ablation probe then sets EOL status, as indicated at 760. Such a status can be determined by the probe electronic circuit due to cessation of therapy delivery, removal of the probe from the patient, or by decoupling of the probe from the ablation generator, for example, as indicated at 762. This then triggers a response at 764, which may be any of generating a visual marker on the ablation probe itself, such as a light or a dye release. A readable indication may also be stored in memory in the electronic circuitry of the probe, which can later trigger an ablation generator which the probe is coupled, to prevent further use of the single use probe.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An ablation probe configured for use with an ablation generator, comprising:
    a distal end having one or more electrodes thereon for delivering therapy directed at target tissue;
    a proximal end having one or more contacts thereon for coupling to the ablation generator;
    an elongated body between the proximal and distal ends carrying at least one conductor that electrically couples at least one electrode to at least one contact;
    a probe electronic circuit in or on the probe and configured to obtain power from the ablation generator and sense one or more characteristics of usage of the probe, quantify the one or more characteristics, and record or transmit data related to the sensed and quantified one or more characteristics; and
    an electronic indicator providing visual feedback to a user of the probe, the electronic indicator being located on the probe and separate from a user interface of the ablation generator, wherein the electronic circuit is coupled to the electronic indicator to allow the data to be displayed to a user via the electronic indicator;
    wherein the electronic circuit obtains power from the ablation generator by harvesting power from therapeutic signals transmitted to the distal end of the probe by the ablation generator via the conductor.

2. The ablation probe of claim 1 wherein the probe electronic circuit is configured so that the one or more characteristics includes end of life of the probe.

3. The ablation probe of claim 1 wherein the probe electronic circuit is configured so that the one or more characteristics includes impedance at or near the distal end of the probe.

4. The ablation probe of claim 1 wherein the probe electronic circuit comprises or is coupled to an antenna for wirelessly transmitting the data.

5. The ablation probe of claim 1 wherein the probe electronic circuit is coupled, via a dedicated conductor, to the probe proximal end, which in turn includes a dedicated contact for enabling the data to be transmitted to the ablation generator.

6. A system comprising the ablation probe of claim 1, and the ablation generator including the user interface, wherein the user interface comprises one of a touchscreen or a monitor.

* * * * *